(12) United States Patent
Rosen et al.

(10) Patent No.: US 10,751,199 B2
(45) Date of Patent: Aug. 25, 2020

(54) TWO-PIECE TOTAL KNEE ROTATION GUIDE AND FEMORAL SIZER SYSTEM AND METHOD

(71) Applicants: Adam Rosen, San Diego, CA (US); Steven Copp, Coronado, CA (US)

(72) Inventors: Adam Rosen, San Diego, CA (US); Steven Copp, Coronado, CA (US)

( * ) Notice: Subject to any disclaimer, the term of this patent is extended or adjusted under 35 U.S.C. 154(b) by 157 days.

(21) Appl. No.: 16/155,748

(22) Filed: Oct. 9, 2018

(65) Prior Publication Data

US 2020/0107942 A1 Apr. 9, 2020

(51) Int. Cl.
*A61F 2/46* (2006.01)
*A61B 17/17* (2006.01)
*A61F 2/38* (2006.01)
*A61B 90/00* (2016.01)

(52) U.S. Cl.
CPC ........ *A61F 2/4657* (2013.01); *A61B 17/1764* (2013.01); *A61F 2/3859* (2013.01); *A61F 2/461* (2013.01); *A61B 2090/061* (2016.02); *A61F 2002/4658* (2013.01)

(58) Field of Classification Search
CPC .......................... A61F 2/4657; A61B 17/1764
See application file for complete search history.

(56) References Cited

U.S. PATENT DOCUMENTS

| | | | |
|---|---|---|---|
| 2005/0203528 A1* | 9/2005 | Couture | A61B 34/20 606/86 R |
| 2005/0251026 A1* | 11/2005 | Stone | A61B 17/175 600/424 |
| 2011/0009868 A1* | 1/2011 | Sato | A61B 17/1764 606/87 |
| 2011/0213375 A1* | 9/2011 | Sikora | A61F 2/389 606/87 |
| 2012/0310246 A1* | 12/2012 | Belcher | A61B 17/155 606/80 |
| 2014/0148811 A1* | 5/2014 | Reeve | A61B 17/155 606/88 |
| 2014/0358151 A1* | 12/2014 | Murphy | A61F 2/4657 606/91 |

* cited by examiner

*Primary Examiner* — Christian A Sevilla
(74) *Attorney, Agent, or Firm* — Procopio Cory Hargreaves and Savitch LLP

(57) ABSTRACT

A two-piece total knee rotation guide and femoral sizer system including a guide that assesses the rotation needed based on the posterior condyles of the femur, and a guide for sizing the femur in the anteroposterior ("AP") dimension.

21 Claims, 5 Drawing Sheets

TWO-PIECE TOTAL KNEE ROTATION GUIDE AND FEMORAL SIZER SYSTEM AND METHOD

FIELD OF THE INVENTION

The present invention relates to a system and method for measuring a patient's femur (thigh bone) in total knee replacement surgery to determine the appropriate size and position for placement during surgery.

BACKGROUND OF THE INVENTION

A total knee replacement is a complex procedure that requires an orthopedic surgeon to make precise measurements and skillfully remove the diseased portions of a patient's bone, in order to shape the remaining bone to accommodate a knee implant. During the surgery, the surgeon makes an incision over the front of the patient's knee to gain access to the joint capsule. A capsulotomy, or incision, is made in the joint capsule to access the knee joint. Once the knee is open, the surgeon moves the patella to the side of the knee to allow the surgeon to visualize the areas needed to perform the surgical procedure. The first bone to be prepared for resurfacing is the patient's femur or thighbone. Once the surgeon has exposed the patient's knee joint, the surgeon carefully measures the patient's bones and makes precise cuts using special instruments. The damaged bone and cartilage from the end of the femur is cut away. The end of the patient's femur is shaped by performing these cuts to fit the first part of the artificial knee, the femoral component. The surgeon then addresses the tibia or shinbone. The surgeon removes damaged bone and cartilage from the top of the tibia and then shapes the bone to fit the metal component that covers the top of the tibia. The bottom portion of the knee implant, called the tibial tray, is then fitted to the tibia and secured into place using bone cement. Once the tray is in place, the surgeon snaps in a polyethylene (medical-grade plastic) insert into the tibial tray to sit between the tibial tray and the femoral component. This tibial insert functions as an efficient artificial bearing surface for the knee. Once the tibia component is cemented in place the femoral part of the implant is cemented to the end of the thigh bone. Before returning the patella to its normal position, the surgeon might need to flatten the patella and fit it with an additional plastic component in order to ensure a proper fit with the rest of the implant. The plastic piece, if needed, is cemented to the underlying bone. The surgeon bends and flexes the knee to ensure that the implant is working correctly, and that alignment, sizing, and positioning is suitable. To complete the procedure, the surgeon will close the joint capsule with stitches and the skin incision with stitches or staples. Bandages are applied and the patient is transferred to the recovery unit.

Total Knee Systems use a conventional instrument or device (FIG. 1) to assess the anteroposterior (AP) size of the femur, determine rotation of the femur, and aid in the positioning of the cutting guide. This device is large, which makes it difficult to use and requires a large incision for exposure and visualization. The current AP sizer includes multiple moving parts which are prone to move and incorrectly size the femur and malposistion the implant. The knee may need to be manipulated, flexed, lifted or moved to allow placement of the device. In smaller incisions, the device can be difficult to use and could potentially lead to misjudging the implant size, placing the patient at risk. The large device, with multiple moving parts can add additional time to the surgical procedure.

SUMMARY OF THE INVENTION

The invention involves a two-piece total knee rotation guide and femoral sizer system used to address these issues. The first piece of the system is a guide that assesses the rotation needed based on the posterior condyles of the femur. This first piece includes separate versions, a guide for the right knee and a guide for the left knee. In the first step, the guide is used to drill holes for pegged systems or the pins can be left in place to slide over in a pinned system. The second piece of the system allows for sizing the femur in the AP dimension. This second piece of the device is pegged for pegged systems and is placed into the peg holes created by the first step. A drill is then used to pass through the guide and distal femur and exit at the location on the top of the femur coinciding with the implant size. This small, second device, which is smaller than similar guides in the past, allows better visualization and allows one to make a more accurate AP measurement. By its smaller size, it fits into smaller knee incisions and places less strain on the soft tissues. With the lack of moving parts it reduces the chance of inaccurate sizing. The appropriate sized pegged 4-in-1 cutting block is then placed into the holes created in the first step.

The slide over version is used by sliding the second piece over the pins that were placed in step one. The remaining steps are the same for determining the size. The appropriate size 4-in-1 cutting block is then placed over the remaining pins. Additional holes in the first piece allow the user to optionally place the holes/pins 1.5 millimeter above or below the standard position. This may be used when the surgeon feels the block should be moved based on the patients' anatomy. The two-piece total knee rotation guide and femoral sizer system and method, with less moving parts, allows total knee replacement surgery to be performed with greater efficiency and potentially better accuracy.

BRIEF DESCRIPTION OF DRAWINGS

The accompanying drawings, which are incorporated in and form a part of this specification illustrate embodiments of the invention and together with the description, serve to explain the principles of the invention.

DESCRIPTION OF EMBODIMENT OF THE INVENTION

Figure 1A:
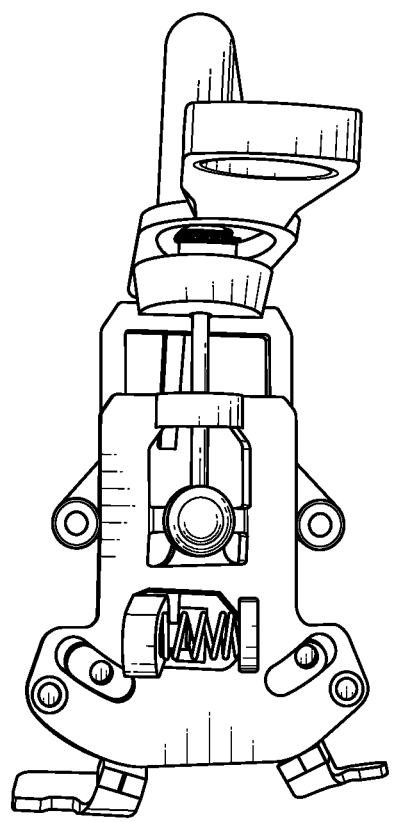
FIG. 1A is a front elevational view of a conventional device used in the past to assess the anteroposterior (AP) size of the femur, determine rotation, and aid in the positioning of a cutting guide during total knee replacement surgery.
Figure 1B:
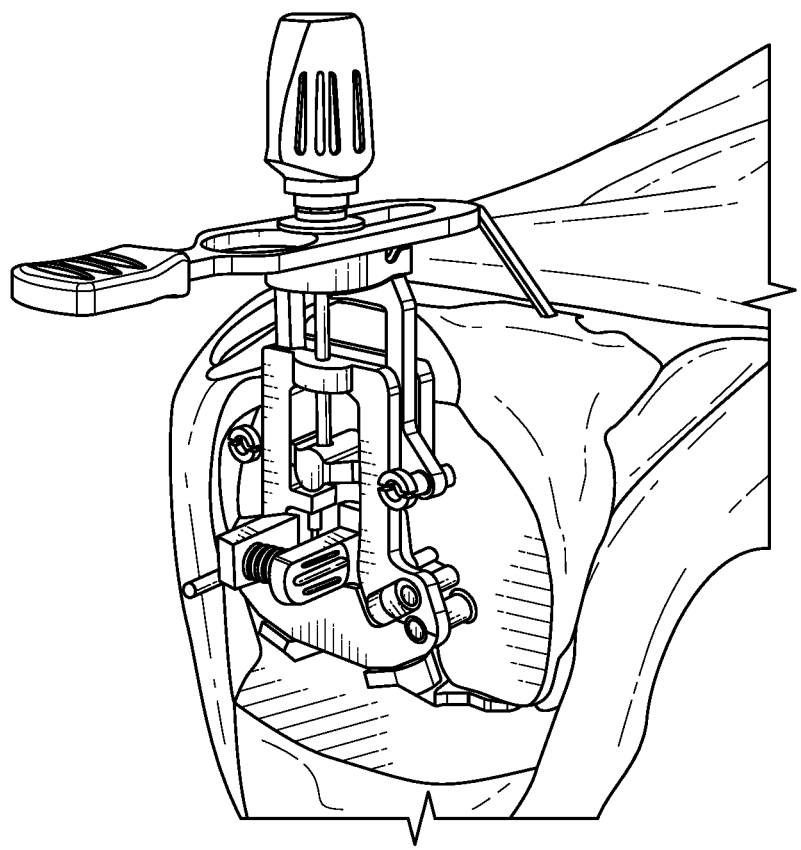
FIG. 1B is a perspective view of the device shown in FIG. 1A shown applied to the end of the femur to assess the anteroposterior (AP) size of the femur.
Figure 2A:
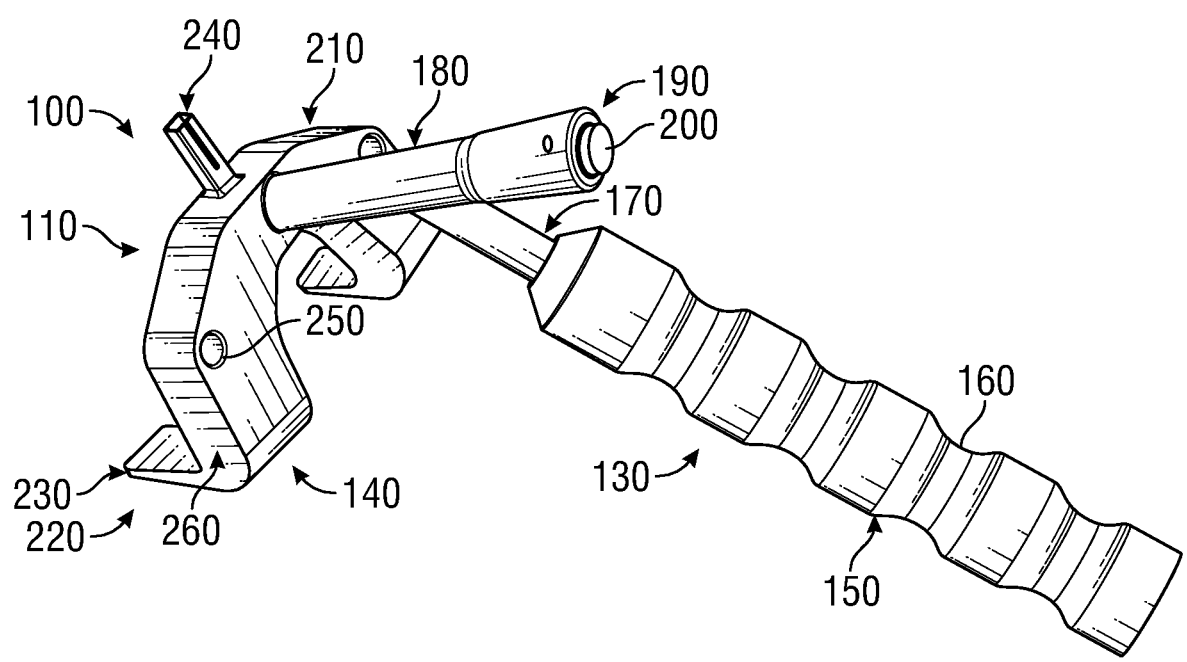
FIG. 2A is a perspective view of an embodiment of a total knee rotation guide of a two-piece total knee rotation guide and femoral sizer system.
Figure 2B:
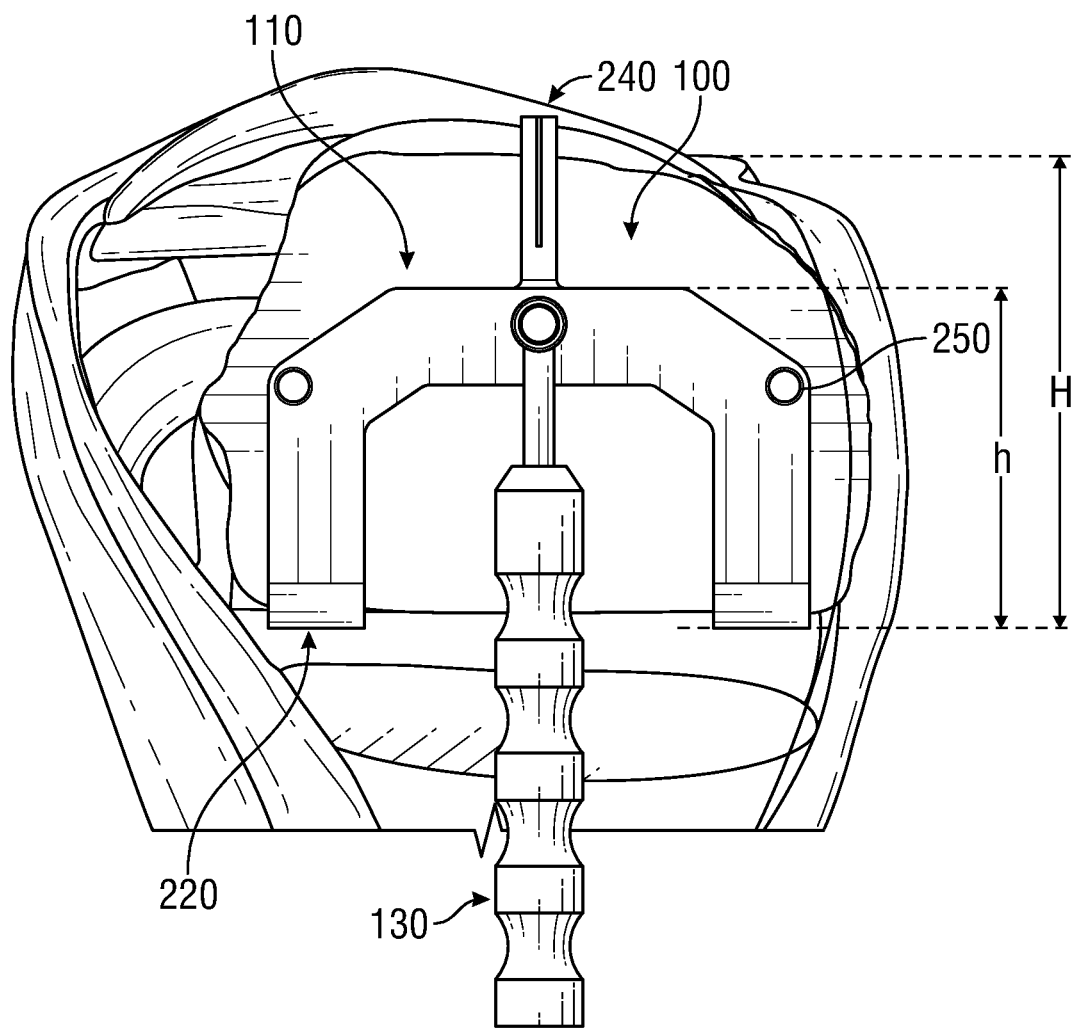
FIG. 2B is a perspective view of the total knee rotation guide of FIG. 2A shown applied to the end of the femur to assess the anteroposterior (AP size of the femur.
Figure 3:
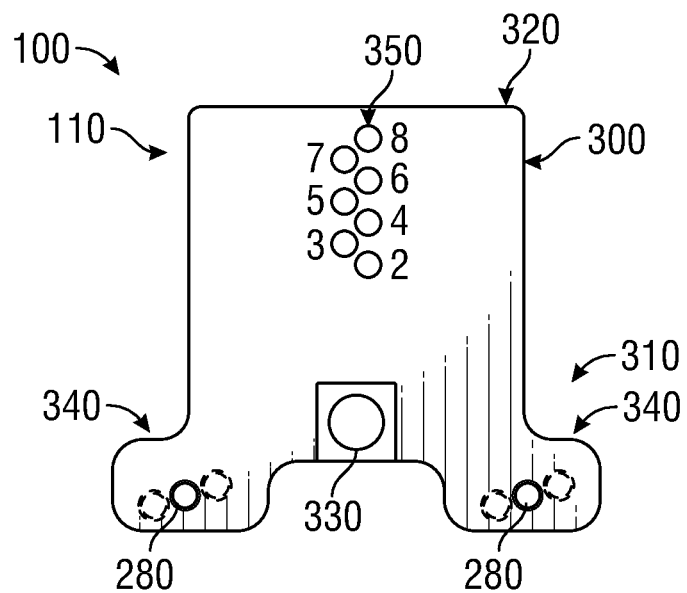
FIG. 3 is front elevational view of an embodiment of a femoral sizer of the two-piece total knee rotation guide and femoral sizer system.

With reference to FIGS. 1-4, an embodiment of a two-piece total knee rotation guide and femoral sizer system 100 and method will be described. The two-piece total knee rotation guide and femoral sizer system 100 includes a total knee rotation guide 110 (FIG. 2A, 2B) and an AP femoral sizing guide 120 (FIG. 3, 4).

The total knee rotation guide 110 is used to determine femoral rotation and sizing after the distal femur has been cut during total knee replacement surgery. The total knee rotation guide 110 includes a removably attachable handle assembly 130 that is removably attachable to a total knee rotation guide assembly 140. The handle assembly 130 includes a grippable handle member 150 with annular recesses 160 therein. The handle member 150 terminates in a stem 170, which is attached at an angle to attachment member 180. This angle is desirably 45 degrees pointed outward to have the handle member 150 out of the way of the holes used for pin placement. The attachment member 180 includes a push button quick release ball, an attachment mechanism 190 including a proximal push-button actuator/deactuator 200 that actuates/deactuates an engagement member (not shown) on an opposite end of the attachment member 180 for removably attaching the total knee rotation guide assembly 140 to the attachment member 180 of the handle assembly 130. The total knee rotation guide assembly 140 is used to assess the rotation needed based on the posterior condyles of the femur. The total knee rotation guide assembly 140 includes separate versions, a total knee rotation guide assembly 140 for the right knee and a total knee rotation guide assembly 140 for the left knee.

The surgeon attaches the handle assembly 130 to and utilizes the appropriate (right or left) guide assembly 140. The guide assembly 140 includes an upside-down U or V shaped bridge 210 that terminates in opposite ends in perpendicularly extending feet 220, which taper in thickness toward distal ends 230. A central portion of bridge 210 includes a hole that receives the attachment member 180 for removably attaching the total knee rotation guide assembly 140 to the attachment member 180 in the manner described above. Extending vertical upward from the bridge 210 is a vertical landmark 240 to assess Whitesides Line, a common landmark used is assessing anatomic rotation during surgery. The bridge 210 includes drill holes 250 in opposite lateral portions 260. The drill holes 250 (i.e. a line through the drill holes 250) are offset 3 degrees counterclockwise from horizontal in the right knee guide assembly 140 and offset 3 degrees clockwise from horizontal in the left knee guide assembly 140; the drill holes 250 are externally rotated 3 degrees (the right knee is rotated counterclockwise and the left knee is rotated clockwise from the user's perspective). As shown in FIG. 2B, the bridge 210 and the opposite lateral portions 260 define an envelope with a height h that is shorter than a height H of the previously resected distal femur that the total knee rotation guide assembly 140 is applied to.

The feet 220 of the guide assembly 140 are placed under the posterior condyles with the bridge 210 flush against the previously resected distal femur. In severe bone loss or loss of cartilage on the posterior condyles, the surgeon may use a shim or augment rotational adjustment, if needed. The distal femur is then marked by placing pins through the two drills holes 250 of the guide assembly 140. In a pegged system, the drill holes are made and the drill is removed. For a pinned system, two pins are placed and left in the femur. The guide assembly 140 is then removed.

Figure 4:
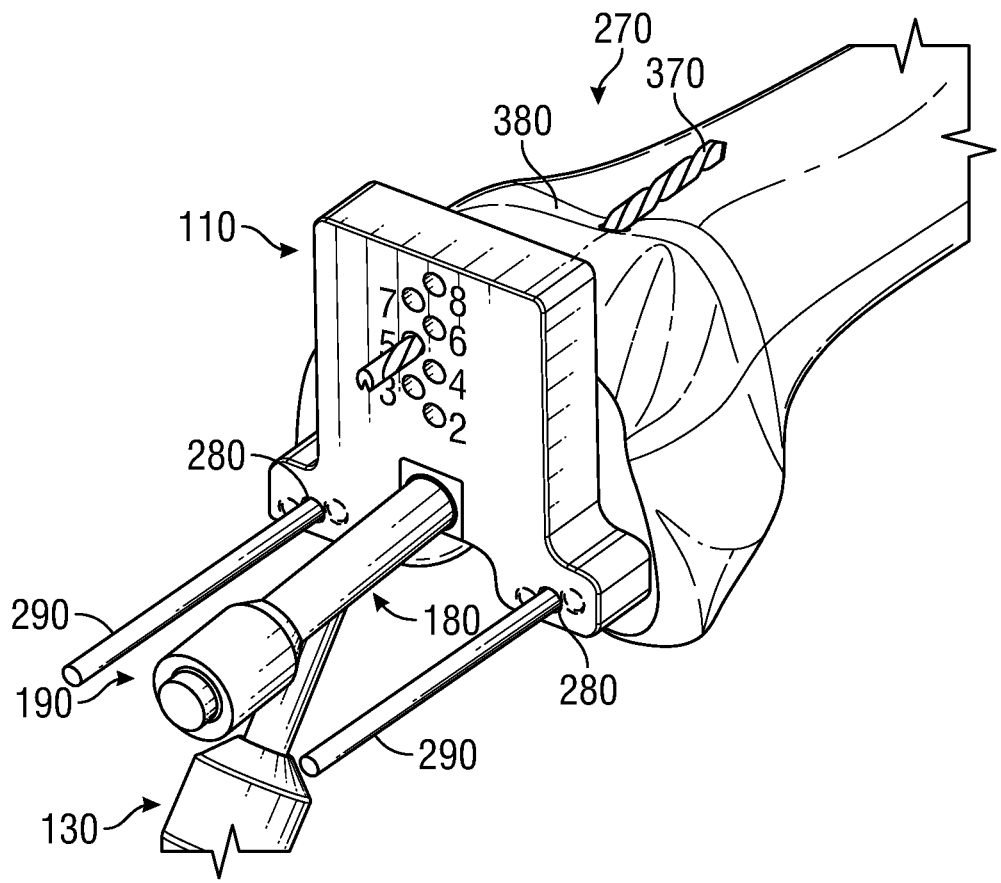
FIG. 4 is a perspective view of the femoral sizer of FIG. 3 and shows the femoral size applied to the distal femur for sizing the distal femur.

With reference to FIGS. 3 and 4, next, the AP femoral sizing guide 120 is placed on distal femur 270, flush with the bone, in alignment with the previously made drill holes. The AP femoral sizing guide 120 is removably attachable to the handle assembly 130 in the manner described above with respect to total knee rotation guide 110 and FIG. 2. In a pegged system/version, the AP femoral sizing guide 120 includes two pegs, which fit in the previously created holes. In a pinned system/version, the AP femoral sizing guide 120 has additional holes 280, which allow the AP femoral sizing guide 120 to slide over pins 290. The AP femoral sizing guide 120 includes a block 300 with a lower portion 310 and an upper portion 320. The lower portion 310 includes a centrally disposed hole 330 that receives the attachment member 180 for removably attaching the AP femoral sizing guide 120 to the attachment member 180 of the handle assembly 130. Opposite sides of the lower portion 310 includes flanges 340 including holes 280. The upper portion 320 includes AP dimension sizing holes 350 for right and left AP femoral sizing. The holes 350 are upwardly inclined at an angle x degrees angled up relative to horizontal, matching an anterior angle (implant specific) of the component. Next, a drill is used to drill a drill bit 370 through the sizing holes 350 of the AP femoral sizing guide 120. The drill bit 370 will exit on an anterior femur 380 in concordance with the appropriate femoral implant size. This will allow accurate size selection of the femoral implant. The holes 350 are labeled for each particular femoral implant size, the drill bit should exit just above the bone which corresponds with where the saw would exit. If the drill is not visible, the cut would notch the bone and the implant would be too small. If there is a large space between the bone and exiting drill bit, the size indicated would be too big.

In a pegged system/version of the AP femoral sizing guide 120, the surgeon may use the optional holes 280 shown in dotted lines to drill two holes 1.5 mm above or below where the standard center holes 280 are shown if it is felt that the 4-in-1 cutting block needs to be moved anterior or posterior 1.5 mm based on the patients' anatomy. It should be noted, in the pegged system/version of the AP femoral sizing guide 120, the center hole would not be a hole, but would have a peg. Thus, only the optional holes 280 shown in dotted lines would be present.

Once the size is determined, the AP femoral sizing guide 120 is removed, the surgeon can place the 4-in-1 cutting block via the pegs into the holes 1.5 mm above or below the standard centered hole to customize the fit. In the pinned system/version of the AP femoral sizing guide 120, the AP femoral sizing guide 120 may not include the additional optional holes 280 because the 4-in-1 cutting block may have the two sets of three holes to slide over the pins, allowing the surgeon to adjust the block anterior or posterior.

Advantages of the two-piece total knee rotation guide and femoral sizer system and method include, but are not limited to, the small AP femoral sizing guide 120, which is smaller than similar guides in the past, allows better visualization to make a more accurate AP measurement; the smaller size of the AP femoral sizing guide 120 fits into smaller knee incisions and places less strain on the soft tissues; and the two-piece total knee rotation guide and femoral sizer system 100 and method, with less moving parts, allow total knee replacement surgery to be performed with greater efficiency.

The above figures may depict exemplary configurations for the invention, which is done to aid in understanding the features and functionality that can be included in the invention. The invention is not restricted to the illustrated architectures or configurations, but can be implemented using a variety of alternative architectures and configurations. Additionally, although the invention is described above in terms of various exemplary embodiments and implementations, it should be understood that the various features and functionality described in one or more of the individual embodiments with which they are described, but instead can be applied, alone or in some combination, to one or more of the other embodiments of the invention, whether or not such embodiments are described and whether or not such features are presented as being a part of a described embodiment. Thus the breadth and scope of the present invention, especially in the following claims, should not be limited by any of the above-described exemplary embodiments.

Terms and phrases used in this document, and variations thereof, unless otherwise expressly stated, should be construed as open ended as opposed to limiting. As examples of the foregoing: the term "including" should be read as mean "including, without limitation" or the like; the term "example" is used to provide exemplary instances of the item in discussion, not an exhaustive or limiting list thereof; and adjectives such as "conventional," "traditional," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, a group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should also be read as "and/or" unless expressly stated otherwise. Furthermore, although item, elements or components of the disclosure may be described or claimed in the singular, the plural is contemplated to be within the scope thereof unless limitation to the singular is explicitly stated. The presence of broadening words and phrases such as "one or more," "at least," "but not limited to" or other like phrases in some instances shall not be read to mean that the narrower case is intended or required in instances where such broadening phrases may be absent.

The invention claimed is:

1. A total knee rotation guide and femoral sizer system, comprising:
a knee rotation guide to assess rotation needed based on posterior condyles of the femur, the knee rotation guide including a rotation guide assembly and a handle assembly removably attachable to the rotation guide assembly, the rotation guide assembly including a bridge and opposite lateral portions extending from the bridge and terminating in opposite ends in perpendicularly extending feet, the rotation guide assembly including drill holes in the opposite lateral portions, the bridge and opposite lateral portions having defining an envelope with a height that is shorter than a height of the previously resected distal femur that the knee rotation guide is applied to;
an anteroposterior (AP) femoral sizing guide comprising an AP femoral sizing guide assembly and a handle assembly removably attachable to the AP femoral sizing guide assembly, the AP femoral sizing guide assembly including a block with a lower portion and an upper portion, the upper portion including AP dimension sizing holes for AP femoral sizing, the AP dimension sizing holes labeled for particular femoral implant sizes and inclined upwardly at an angle relative to horizontal, matching an anterior angle of a particular femoral implant.

2. The total knee rotation guide and femoral sizer system of claim 1, wherein the handle member terminates in a stem, and the knee rotation guide further includes an attachment member that the stem is attached to.

3. The total knee rotation guide and femoral sizer system of claim 2, wherein the attachment member includes an attachment mechanism including a proximal push-button actuator to removably attach the rotation guide assembly to the attachment member.

4. The total knee rotation guide and femoral sizer system of claim 1, wherein the perpendicularly extending feet taper in thickness toward distal ends.

5. The total knee rotation guide and femoral sizer system of claim 1, wherein the drill holes are offset 3 degrees from horizontal.

6. The total knee rotation guide and femoral sizer system of claim 1, wherein the knee rotation guide includes a right knee version or a left knee version.

7. The total knee rotation guide and femoral sizer system of claim 1, wherein the AP femoral sizing guide is a pinned version with the lower portion including opposite sides with flanges having holes that receive pins placed in previously drilled holes.

8. The total knee rotation guide and femoral sizer system of claim 1, wherein the AP femoral sizing guide is a pegged version with two pegs that are received in previously drilled holes.

9. The total knee rotation guide and femoral sizer system of claim 8, wherein the AP femoral sizing guide further comprises holes of the flanges including standard center holes and holes above and below the standard center holes to drill above or below the standard center holes if the AP femoral sizing guide and two pegs need to be moved anterior or posterior based on a patient's anatomy.

10. A method of using the total knee rotation guide and femoral sizer system of claim 1, comprising:
using the knee rotation guide to drill holes in the resected distal femur for placement of pins for a pinned AP femoral sizing guide or placement of pegs for a pegged AP femoral sizing guide;
applying the anteroposterior AP femoral sizing guide to the resected distal femur using the pins or the pegs;
drilling through one or more of the AP dimension sizing holes;
determining AP femoral sizing corresponding to the AP dimension sizing hole drilled through where the drill bit exits just above the bone on an anterior femur.

11. The method of claim 10, wherein the AP femoral sizing guide is a pegged version and the AP femoral sizing guide further comprises holes of flanges including standard center holes and holes above and below the standard center holes, and the method further including drilling above or below the standard center holes if the AP femoral sizing guide and two pegs need to be moved anterior or posterior based on a patient's anatomy, and moving and the AP femoral sizing guide and two pegs anterior or posterior.

12. The method of claim 11, further including placing a determined size cutting block and pegs into the holes created in the resected distal femur.

13. The method of claim 10, further including sliding a determined size cutting block over previously placed pins in the resected distal femur.

14. An anteroposterior (AP) femoral sizing guide, comprising:
an AP femoral sizing guide assembly; and
a handle assembly removably attachable to the AP femoral sizing guide assembly
wherein the AP femoral sizing guide assembly includes a block with a lower portion and an upper portion, the upper portion including AP dimension sizing holes for AP femoral sizing, the AP dimension sizing holes labeled for particular femoral implant sizes and inclined upwardly at an angle relative to horizontal, matching an anterior angle of a particular femoral implant.

15. The AP femoral sizing guide of claim 14, wherein the AP femoral sizing guide is a pinned version with the lower portion including opposite sides with flanges having holes that receive pins placed in previously drilled holes.

16. The AP femoral sizing guide of claim 14, wherein the AP femoral sizing guide is a pegged version with two pegs that are received in previously drilled holes.

17. The AP femoral sizing guide of claim 16, wherein the AP femoral sizing guide further comprises holes of flanges including standard center holes and holes above and below the standard center holes to drill above or below the standard center holes if the AP femoral sizing guide and two pegs need to be moved anterior or posterior based on a patient's anatomy.

18. A method of using the AP femoral sizing guide of claim 14 where holes in resected distal femur have been previously drilled for placement of pins for a pinned AP femoral sizing guide or placement of pegs for a pegged AP femoral sizing guide, comprising:
applying the anteroposterior AP femoral sizing guide to the resected distal femur using the pins or the pegs;
drilling through one or more of the AP dimension sizing holes;
determining AP femoral sizing corresponding to the AP dimension sizing hole drilled through where the drill bit exits just above the bone on an anterior femur.

19. The method of claim 18, wherein the AP femoral sizing guide is a pegged version and the AP femoral sizing guide further comprises holes of flanges including standard center holes and holes above and below the standard center holes, and the method further including drilling above or below the standard center holes if the AP femoral sizing guide and two pegs need to be moved anterior or posterior based on a patient's anatomy, and moving and the AP femoral sizing guide and two pegs anterior or posterior.

20. The method of claim 18, further including placing a determined size cutting block and pegs into the holes created in the resected distal femur.

21. The method of claim 18, further including sliding a determined size cutting block over previously placed pins in the resected distal femur.

* * * * *